United States Patent [19]

Blach

[11] Patent Number: 4,686,370

[45] Date of Patent: Aug. 11, 1987

[54] IONIZING CHAMBER FOR GASEOUS OXYGEN

[75] Inventor: Thomas Blach, Buxtehude, Fed. Rep. of Germany

[73] Assignee: Biomed-Electronic GMBH & Co. Med:2:N:schor Geratebau KG, Buxtehude, Fed. Rep. of Germany

[21] Appl. No.: 700,777

[22] Filed: Feb. 13, 1985

[30] Foreign Application Priority Data

Feb. 13, 1984 [DE] Fed. Rep. of Germany ....... 3405008
Mar. 28, 1984 [DE] Fed. Rep. of Germany ....... 3411335

[51] Int. Cl.$^4$ .............................................. H01J 27/00
[52] U.S. Cl. .............................. 250/423 R; 313/360.1
[58] Field of Search ................. 250/423 R, 288; 313/359.1, 360.1, 362.1; 315/111.81

[56] References Cited

U.S. PATENT DOCUMENTS

| | | | |
|---|---|---|---|
| 3,668,385 | 6/1972 | Cohen | 250/288 |
| 4,178,877 | 12/1979 | Kudo | 250/423 R |
| 4,521,719 | 6/1985 | Liebel | 313/360.1 |

FOREIGN PATENT DOCUMENTS

| | | |
|---|---|---|
| 1261295 | 2/1968 | Fed. Rep. of Germany . |
| 2120397 | 11/1971 | Fed. Rep. of Germany . |
| 2545905 | 6/1979 | Fed. Rep. of Germany . |
| 1509410 | 10/1974 | United Kingdom . |

OTHER PUBLICATIONS

"Hinweise für die Benutzung" Römpps Chemie-Lexikon/Otto Albrecht Neumüller–Stuttgart 1983, excerpt from Library of Congress cataloging in Publication Data 1977.

Primary Examiner—Bruce C. Anderson
Attorney, Agent or Firm—Karl F. Ross, Herbert Dutno

[57] ABSTRACT

An ionization chamber for producing oxygen ions, preferably positive oxygen ions, without substantial ozone formation. The housing can be composed of polyvinyl chloride or another insulating material and the ionization electrodes can include a cathode wire closed to the inlet and an anode wire downstream from the cathode wire, the wires extending transverse to the oxygen flow direction.

17 Claims, 7 Drawing Figures

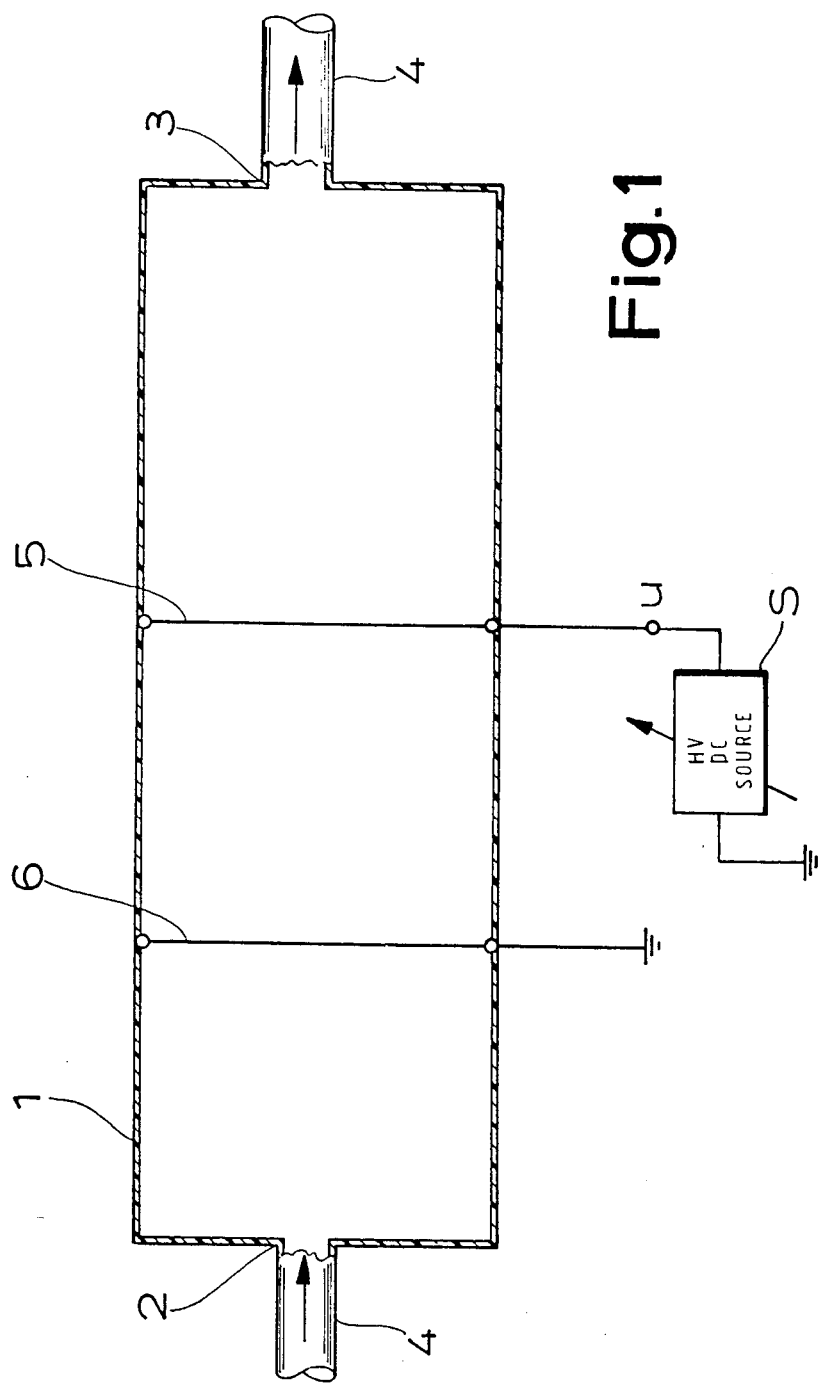

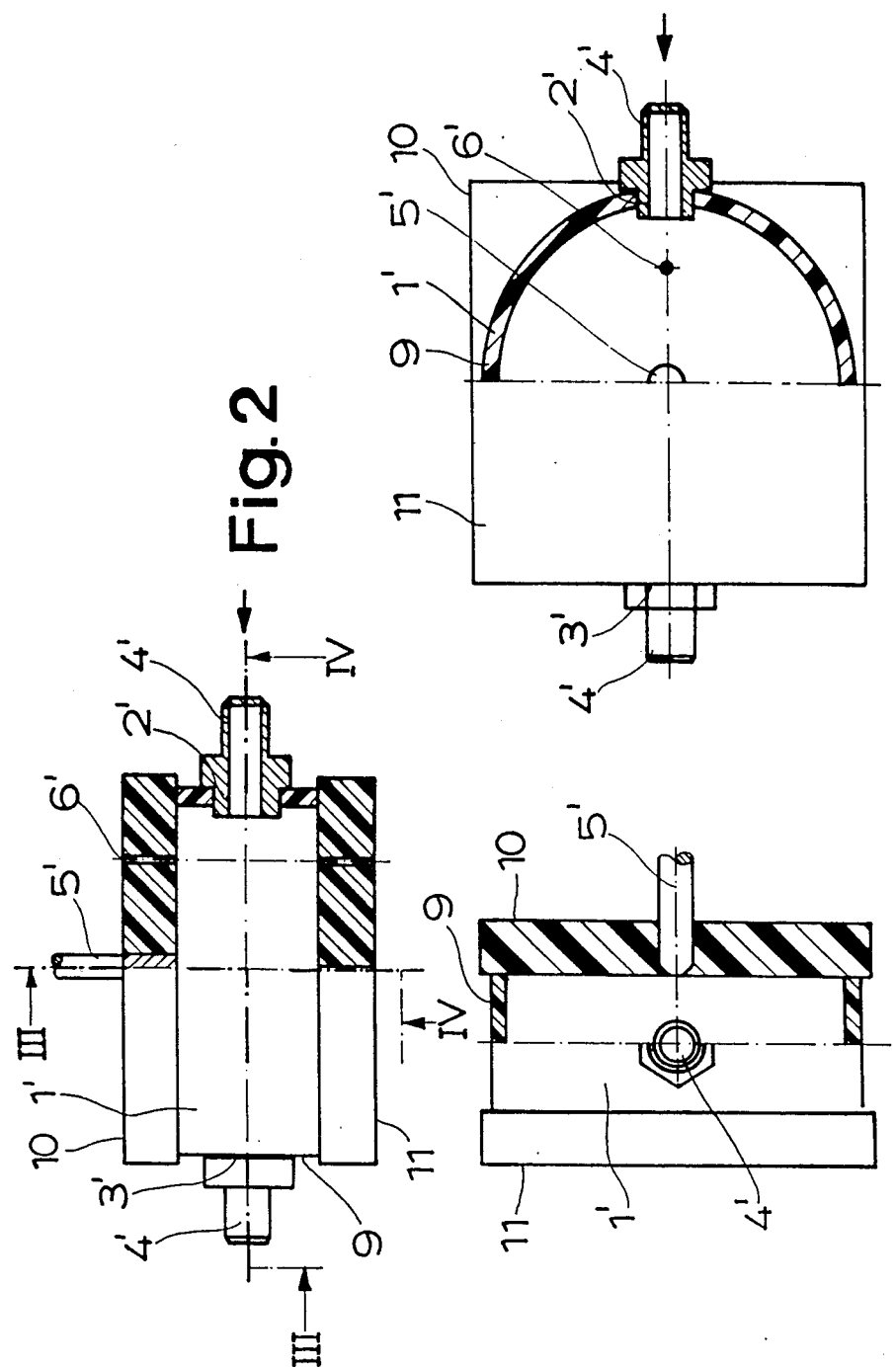

IONIZING CHAMBER FOR GASEOUS OXYGEN

FIELD OF THE INVENTION

My present invention relates to an ionization chamber for the ionization of gaseous oxygen and, more particularly, to a chamber for generating ions in a medium containing $O_2$ for medicinal, therapeutic or general well-being improvement.

BACKGROUND OF THE INVENTION

Ionization chambers for a flowing medium to be ionized are, of course, known and generally comprise an elongated cylindrical housing traversed longitudinally by the gas stream and, therefore, having an inlet end for the gas stream to be ionized, an outlet end for the gas stream to be discharged, and, within this chamber an anode and a cathode generally connected to a direct current source.

The anode in a conventional ionization chamber of this type generally is a wire extending centrally through this chamber in the longitudinal direction, i.e. is usually disposed along the axis of the chamber and can be a rod if desired. The cathode, however, is usually a cylindrical shell which is coaxial with the anode and can be formed by the housing wall itself. In either case the medium flows parallel to the anode and the cathode (See Holleman, Wiberg: "Lehrbuch der anorganischen Chemie", Berlin, 1964, page 178).

Ionization of a flowing medium may be practiced for a variety of reasons and hence the discussion here will concentrate on atmospheric air or pharmaceutical grade oxygen as the flowing medium to be ionized. When room air, oxygen-enriched air or even pure oxygen is ionized, it contributes to a variety of therapeutic processes and also in general, to the well-being of persons subject to the ionized oxygen. Many investigations have shown that the ion concentration of room air has a significant effect upon the emotional states of individuals present in the room and, in general, with elevated ion concentrations, individuals feel healthier, more active, and for the most part, satisfied and happy. Excessively low ion concentrations, however, contribute to a general feeling of malaise (see Lueger: "LEXIKON DER TECHNIK", Band 6, "Lexikon der Energietechnik und Kraftmaschinen" DVA, Stuttgart, 1965, pages 90 and 91, keyword "Behaglichkeit (Wohlbefinden)").

Apart from the use of ionization devices in personnel-occupied rooms to impart a general feeling of well-being, a number of therapeutic uses for highly ionized gaseous oxygen have been developed, and indeed, respiration therapy using gaseous oxygen with ionization is of considerable significance for various therapeutic treatments.

Ionization of gaseous oxygen utilizing the ionization chamber described above can give ion concentrations up to about 15,000 ions/cm$^3$, However, simultaneously with the generation of such ions, there is a significant production of ozone ($O_3$). This is a crucial disadvantage, especially for medicinal applications of ionized oxygen or air, because ozone in significant concentrations has a corrosive effect on the respiratory organs.

OBJECTS OF THE INVENTION

It is, therefore, the principal object of the present invention to provide an ionization chamber in which high ion concentrations of oxygen can be produced and in which, indeed, the carrier can have significantly increased oxygen ion concentration while avoiding the production of ozone.

Another object of this invention is to provide an improved method of generating high concentrations of ionized oxygen in a gas stream with minimum formation of ozone.

It is also an object of this invention to provide an improved method of producing oxygen ions in high concentrations and an ionization chamber for this purpose whereby disadvantages of prior art ionization chambers can be avoided.

SUMMARY OF THE INVENTION

These objects and others which will become apparent hereinafter are attained, in accordance with the present invention, which provide an ionization chamber in the form of an elongated preferably cylindrical housing formed with an inlet end connected to a source of an oxygen-containing gas and an outlet end connected to means for discharging an ionized-oxygen stream and a pair of elongated electrodes electrically insulated from one another and extending in this chamber in spaced-apart relationship and transversely to the flow direction of the oxygen stream, these electrodes being connected to a source of direct current so that one can be considered to be the anode while the other is a cathode. Essential to the invention, moreover, is that these electrodes be spaced apart in the direction of flow of the oxygen-containing gas in addition to being transverse to the flow direction.

The term anode and cathode and electrodes generally can refer to wires or rods.

Surprisingly I have found that with this orientation of the anode and cathode, ion concentrations of up to 1,500,000 ($1.5 \times 10^6$) ions/cm$^3$ can be achieved or that charge-carrier concentrations (in more general terms) of such levels can be reached.

The difference between the oxygen ion concentration and the charge carrier concentration is a result of the fact that while positively-charged oxygen atoms form true ions in a sense of an ion concentration, the negative-charge carrier may be negatively charged oxygen, free electrons or free electrons associated with gas molecules or other atoms. There are, therefore, additional charge carriers which may be present.

For the ionization of oxygen, generally, it is the positive ions which are significant for medicinal or therapeutic purposes.

It has been found, surprisingly, that with the ionization chamber of the invention an especially strong ionization in terms of the high production of positive ions can be achieved without ozone formation.

Apparently with the arrangement of the present invention of the anode and the cathode, the interaction between the oxygen molecule and the electric field is sufficiently intense to obtain a maximum ionization effect but the energy level and time of contact are insufficient to bring about the formation of atomic oxygen which is a necessary precursor (by its combination with $O_2$) in the formation of ozone.

I have already indicatd that it is of paramount importance that the ionization chamber produce a high concentration of positively ionized oxygen.

For this reason I have found it to be advantageous to provide the anode behind the cathode in the direction of flow of the medium, i.e. downstream from the cathode.

Apparently this ensures that free electrons or negative charges can be collected upon and conducted away from the anode at a downstream location while the positive oxygen ions, because of their large mass and hence momentum are not drawn back to the cathode in spite of the electrical field gradient which exerts an electrostatic force in this direction.

Naturally, the cathode should be provided downstream of the anode when a gas stream containing high concentrations of negatively ionized oxygen is desired.

It has been found to be advantageous to provide the cathode as a reference electrode with a fixed reference potential, for example as a ground electrode (PE-electrode) and to vary only the potential with respect to ground of the anode when variation is required.

There are, of course, numerous ways in which the principles set forth above can be realized. The anode and cathode, for example, can be simply stretched across the chamber as single wires in respective planes perpendicular to the axis of the chamber and transverse to the flow direction. The anode and cathode can also be formed by arrays of wires lying in these planes and even a grid of wires.

For the ionization of oxygen, however, I have found that copper wire is preferred.

One of the surprising things which has been learned from this invention is that the question of ionization of oxygen without ozone formation is only a question of the exchange effect or interaction of the flowing action with the electric field.

The field strength of the electrical field is determined by the potential between anode and cathode on the one hand and the geometric structure of the anode and the cathode, namely the field-line density on the other. It is possible that it is the latter factor which explains the surprising result, i.e. the prevention of ozone formation. Apparently the field lines and organization are such that even at potentials which would have generated ozone with the prior art ionization chamber, ozone formation is precluded here.

It has been found to be advantageous that the anode and cathode forming wires, preferably of copper, each be provided with a coating of a lacquer.

The ignition potential of the ionization chamber of the invention, i.e. the potential at which a breakdown occurs and ionization commences, can be reduced and ozone formation precluded even further when the anode and the cathode are disposed substantially midway of the oxygen flow, i.e. in a plane perpendicular to the aforementioned transverse plane along the axis of the chamber.

The ignition potential can also be reduced by stepping one or both of the electrodes, i.e. providing the anode and cathode substantially in the region of the center of the stream with a step in a plane perpendicular to the low direction of the stream. The stepping can include on each wire only a single upwardly or downwardly extending step or two steps, i.e. upwardly and then downwardly or vice versa. Naturally, the number of steps can be increased and can extend along the length of the wire, for example, has an undulating, corrugated or wave shape.

Apparently this modification from the rectilinear or straight line paths of the wires disrupts the field lines to the point that the ignition potential is reduced.

Of course, since it is desirable to avoid high field intensities, it is important while providing the steps to observe the condition that the wires should be free from sharp edges or corners or points and that, as a consequence of bends in the formation of such steps, should have a radius of curvature of at least 1.5 mm.

Additionally, the steps or bends of the anode and cathode should extend in opposite directions so that any projection the outlines of these steps in the flow direction of the gas form a framelike opening. This has been found to give an exceptionally low ozone formation.

The distance between inlet opening and the proximal electrode, preferably the cathode, should be between 5 and 20 mm, preferably between 10 and 15 mm. This allows optimum utilization of the electric field in the ionization chamber. The closest spacing between the anode and the cathode should preferably be between 10 and 50 mm and most advantageously between 20 and 30 mm.

The diameters of the electrode wires forming the anode and the cathode should be 0.2 to 1.0 mm, advantageously 0.3 to 0.7 mm and most preferably about 0.4 mm. This ensures an optimal construction without excessive electrical field strength although it should be noted that the field strength also is a function of the lacquer thickness which may be applied in a coating having a thickness of say 2 microns.

Best results are obtained when the cathode is at ground potential and the anode is at a positive potential relative to ground (direct current) of at most 10 kV.

The housing of the ionization chamber can be fabricated from an electrically nonconducting material, for example a synthetic resin such as polyvinylchloride (PVC), a material which is particularly advantageous because of its high electrical dielectric strength, i.e. resistance to breakdown, its reduced tendency to sustain creepage currents along its surface, its limited antistatic characteristics and its excellent surface finishing and shaping possibilities while having a relatively low cost.

From the choice of this material the conditions under which housing materials may be selected will also be apparent, i.e. the housing material should suffer from a minimum of electrical creepage current, should have a high dielectric strength and limited antistatic characteristics.

The specific construction of the housing can enable it to be elongated in the flow direction or, in a particularly advantageous embodiment of the invention, to be formed with a cylindrical body closed at its ends by respective plates. The inlet opening and the outlet opening are formed in a cylindrical body opposite one another while the anode and cathode extend through the cylindrical body and are anchored in these plates, the electrodes being parallel generally to one another and to the axis of the cylindrical body.

A multiplicity of such ionization chambers can be assembled into a multicompartment ionization chamber and thus two such ionization chambers can be provided in the form of a double chamber although generally the number which will be assembled into a unit will be greater than two. The number of ionization chambers used will depend upon the use to which the assembly is to be put and because of the field conditions, in general, a number of small ionization chambers is more effective than a single large ionization chamber when the apparatus is divided into a number of ionization chambers, each anode and cathode can extend through a number of chambers.

BRIEF DESCRIPTION OF THE DRAWING

The above and other objects, features and advantages of the present invention will become more readily apparent from the following description, reference being made to the accompanying drawing in which:

FIG. 1 is a schematic cross section through an ionization chamber according to the invention;

FIG. 2 is an elevational view through an ionization chamber according to another embodiment of the invention, particularly in axial section;

FIG. 3 is a section taken along the line III—III of FIG. 2;

FIG. 4 is a section taken generally along the line IV—IV of FIG. 2;

SPECIFIC DESCRIPTION

Figure 5:
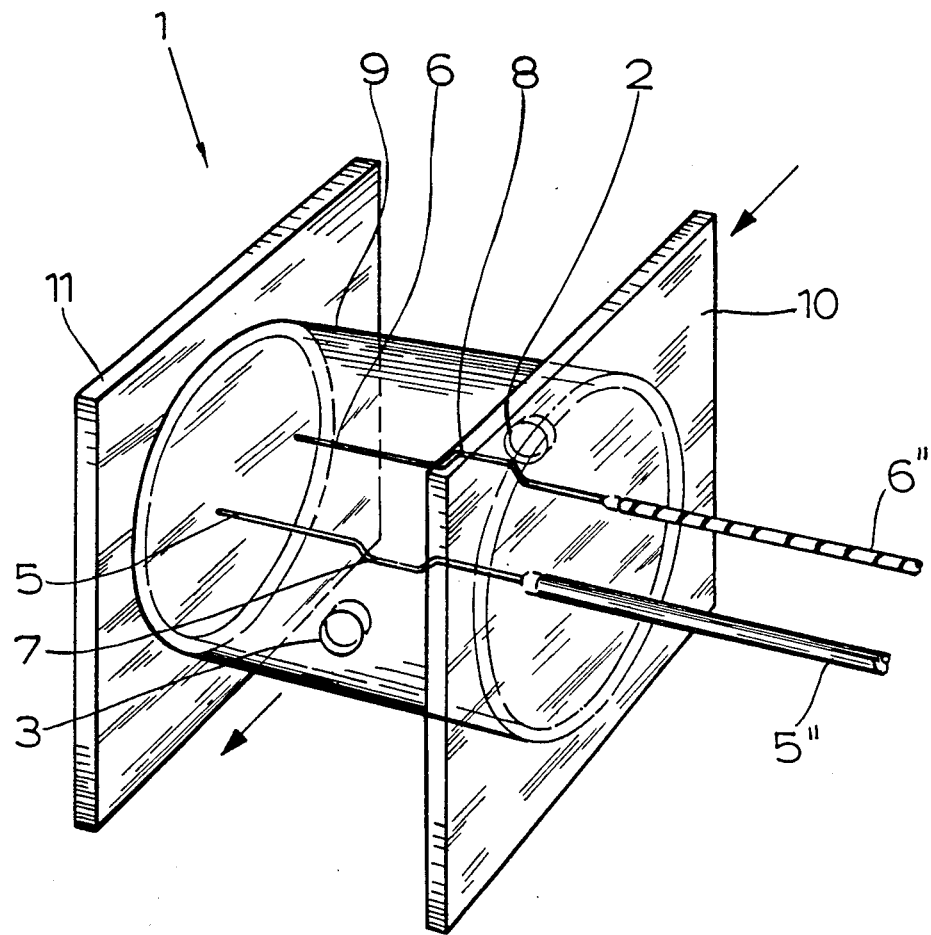
FIG. 5 is a perspective view of another embodiment of the invention.

FIG. 1 shows the principles of the present invention.

The ionization chamber illustrated here is used for ionizing gaseous oxygen and comprises a housing 1 composed of polyvinyl chloride or a like insulating material and is connected with an inlet pipe 4 for the gas stream at an inlet opening 2. Another pipe 4 is connected to the outlet opening 3 which is opposite the inlet opening.

Thus the gas flows in the direction of the arrow.

Within the housing 1, I provide a pair of electrodes 5, 6 which are connected to a high voltage dc source S. The electrodes include an anode 5 and a cathode 6. As is clear from this Figure, the anode 5 and the cathode 6 extend transversely to the direction of flow of the oxygen stream and are spaced apart in the direction of flow with the anode 5 being located further downstream than the cathode 6. Positive ions are discharged from the outlet 3.

FIG. 1 also shows that the anode and cathode can be wires which are preferably composed of copper, can be coated with a lacquer layer and can be a diameter of about 0.4 mm.

In the particular arrangement shown, the cathode 6 is grounded as is one terminal of the high voltage direct current source S which is adjustable to apply a positive potential ranging between 0 to 10 kV relative to ground to the anode 5.

FIGS. 2–4 show an embodiment of the invention in which a cylindrical body 1' forms the ionization chamber between a pair of plates 10 and 11, a pair of diametrically opposite fittings 2' and 3' forming the inlet and outlet openings, respectively, and being connectable to pipe sections 4' to which plastic or rubber tubes can be connected, the inlet 2 being supplied by a pump, for example. The anode 5' and the cathode 6' are represented only diagrammatically in these Figures. The flow direction is again represented by the arrows and it can be seen that the cathode 6' is located relatively upstream while the anode 5' is located relatively downstream and that both electrodes extend across the flow, i.e. transversely to the flow.

The cathode 6' is preferably spaced about 10 mm from the inlet opening 2' and the anode 5' is preferably spaced about 20 mm from the cathode 6'. The housing 1' and the plates 10, 11 are here constituted of polyvinyl chloride. the cylindrical housing or body 1' has been represented at 9.

FIG. 5 illustrates another embodiment of the invention which differs from that of FIGS. 2–4 in tht the anode 5" and the cathode 6" substantially in the middle of the flow of oxygen are bent to form steps in vertical planes perpendicular to the flow direction, the bend of the cathode 6" being upwardly and then downwardly while the bend of the anode 5" is initially downwardly then upwardly, the steps being represented at 7 and 8. Each bend is carefully made to ensure that it has a radius of curvature of at least 1.5 mm.

The steps introduce an inhomogeneity of the electrical field between the anode and cathode so that the discharge potential of the ionization chamber is reduced although the curvatures are such that excessively high field strengths do not develop and ozone formation is reduced.

It can be seen from FIG. 5 that the steps 7 and 8 lie in mutually parallel planes but are in opposite directions so that a projection of these steps on a plane in the direction of oxygen flow defines a framelike opening in the form of an elongated window. This has been found to be important for optimal ionization without the formation of ozone in a number of tests.

In the embodiments of FIGS. 2–5 the housing is basically formed by a cylindrical body closed with plates at its ends and having the inlets and outlets in the housing body so that the anode and cathode are generally parallel to one another and to the axis of the cylindrical body.

The electrodes can be isolated from the housing when the housing conductive with conventional polyurethane insulation for the cathode 6 or for the grounded electrode and with any high voltage insulation for the other electrode which may be at a positive or negative potential with respect to ground.

Figure 6:
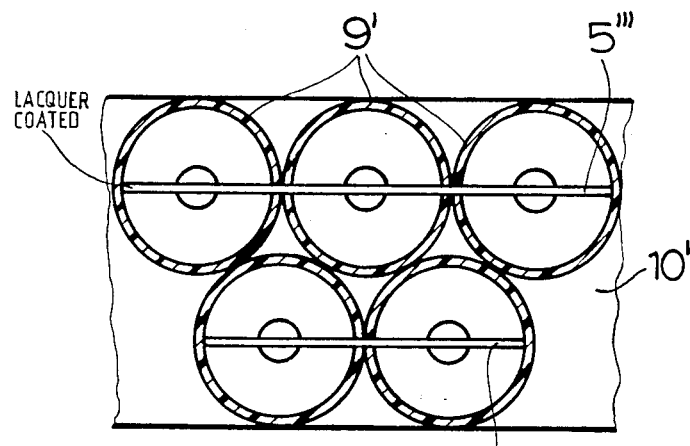
FIG. 6 is a transverse cross-sectional view through yet another embodiment.
Figure 7:
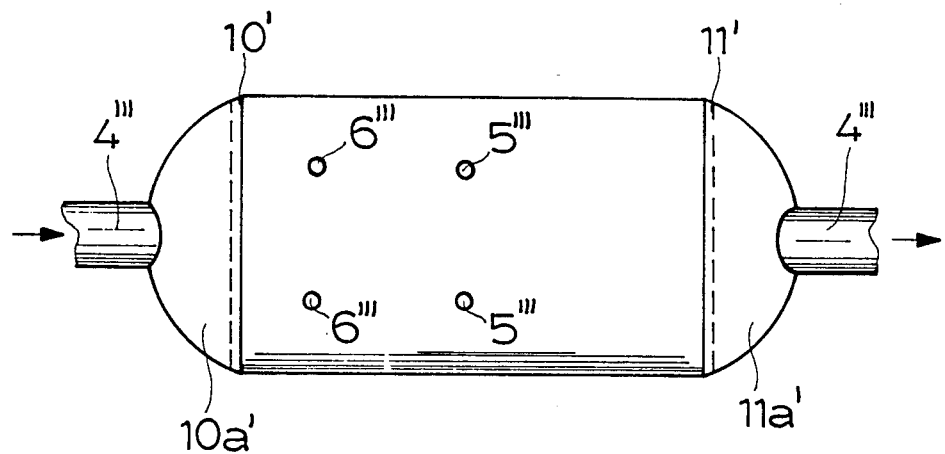
FIG. 7 is a side elevational view of this latter embodiment.

FIGS. 6 and 7 show an embodiment of the invention in which the cylindrical bodies 9' are joined together, e.g. by adhesive and closed at the respective ends by a pair of plates 10' and 11' which are spanned by the cathode and anode wires 6''' and 5''', respectively. As is also apparent from FIG. 6, each anode and cathode wire extends through a group of ionization chambers, i.e. through the individual cells of the ionization apparatus.

The plates 10' and 11' are supplied by manifolds or domes 10a' amd 11a' connected to the pipes 4'''.

I claim:

1. An ionization chamber for the ionization of gaseous oxygen in a gas stream, comprising a housing formed with an inlet for said stream and an outlet for ionized oxygen and traversed by said stream in a given direction between said inlet and said outlet, a pair of electrodes mounted in said housing and extending across said stream transverse to said flow direction with said electrodes spaced apart in said direction and at least one of said electrodes formed from a copper wire provided with a lacquer coating, and a direct current source connected across said electrodes whereby one of said electrodes forms an anode and another of said electrodes forms a cathode.

2. The ionization chamber defined in claim 1 wherein said anode is located downstream of said cathode.

3. The ionization chamber defined in claim 1 wherein said cathode is at a fixed reference potential and said anode is connected to said source and receives a variable potential relative to said cathode.

4. The ionization chamber defined in claim 3 wherein said cathode is connected to ground potential.

5. The ionization chamber defined in claim 1 wherein each of said electrodes is formed substantially in the middle of said stream with a step lying in a plane perpendicular to said direction.

6. The ionization chamber defined in claim 5 wherein all bends of each electrode forming said step have radii of curvature of at least 1.5 mm.

7. The ionization chamber defined in claim 5 wherein said steps extend in opposite directions from one another.

8. The ionization chamber defined in claim 1 wherein the spacing between said cathode and said inlet is substantially 5 to 20 mm.

9. The ionization chamber defined in claim 10 wherein the spacing of said anode from said cathode is substantially 10 to 50 mm and said anode is located downstream of said cathode.

10. The ionization chamber defined in claim 11 wherein said electrodes are wires of a diameter of 0.2 to 1.0 mm.

11. The ionization chamber defined in claim 10 wherein the spacing of said cathode from said inlet is between 10 and 15 mm, the spacing of said anode from said cathode is between 20 and 30 mm and the diameter of said electrodes is between 0.3 and 0.7 mm.

12. The ionization chamber defined in claim 11 wherein said diameter is substantially 0.4 mm.

13. The ionization chamber defined in claim 12 wherein said source has a potential sufficient to generate oxygen ions less than 10 kV and is a variable potential source.

14. The ionization chamber defined in claim 1 wherein said housing is composed of polyvinyl chloride.

15. The ionization chamber defined in claim 1 wherein said housing has a cylindrical body formed with said inlet and said outlet and closed at its ends by a pair of plates and said body spanned by said electrode.

16. The ionization chamber defined in claim 1 wherein a multiplicity of said chambers are assembled together in parallel to form respective cells.

17. The ionization chamber defined in claim 18 wherein a plurality of said cells are traversed by the same said electrodes.

* * * * *